(12) United States Patent
Kubo et al.

(10) Patent No.: US 10,653,858 B2
(45) Date of Patent: May 19, 2020

(54) CATHETER AND BALLOON CATHETER

(71) Applicant: ASAHI INTECC CO., LTD., Seto-shi, Aichi (JP)

(72) Inventors: Yuta Kubo, Seto (JP); Takeharu Katsurada, Nagoya (JP); Moritaka Ogido, Seto (JP)

(73) Assignee: ASAHI INTECC CO., LTD., Seto-shi (JP)

( * ) Notice: Subject to any disclaimer, the term of this patent is extended or adjusted under 35 U.S.C. 154(b) by 451 days.

(21) Appl. No.: 15/204,129

(22) Filed: Jul. 7, 2016

(65) Prior Publication Data

US 2017/0043119 A1 Feb. 16, 2017

(30) Foreign Application Priority Data

Aug. 10, 2015 (JP) .................. 2015-157962

(51) Int. Cl.
*A61M 25/00* (2006.01)
*A61M 25/10* (2013.01)

(52) U.S. Cl.
CPC .......... *A61M 25/005* (2013.01); *A61M 25/10* (2013.01)

(58) Field of Classification Search
CPC ........ A61M 25/09; A61M 2025/09083; A61M 2025/09133; A61M 25/005; A61M 25/0012; A61M 25/0021; A61M 25/0043; A61M 25/0045
See application file for complete search history.

(56) References Cited

U.S. PATENT DOCUMENTS

| | | | | |
|---|---|---|---|---|
| 3,926,705 A | * | 12/1975 | Todd | A61M 25/0015 156/155 |
| 3,935,139 A | * | 1/1976 | Ashall | C08G 8/00 524/594 |
| 3,980,453 A | * | 9/1976 | Fukuda | B24D 18/00 51/297 |

(Continued)

FOREIGN PATENT DOCUMENTS

| EP | 1 721 631 A1 | 11/2006 |
|---|---|---|
| EP | 2 762 187 A1 | 8/2014 |

(Continued)

OTHER PUBLICATIONS

Jan. 9, 2017 Extended European Search Report issued in European Patent Application No. 16177043.3.

(Continued)

*Primary Examiner* — Quynh-Nhu H. Vu
(74) *Attorney, Agent, or Firm* — Oliff PLC

(57) ABSTRACT

A catheter includes a tubular inner layer, a reinforcement body disposed around the outer periphery of the inner layer, a protective layer covering the outer periphery of an end of the reinforcement body, and an outer layer covering at least the outer periphery of the protective layer. The protective layer covers the outer periphery of at least one end of reinforcement body, and the end of the reinforcement body covered with the protective layer is buried deeper in a side of the inner layer relative to a portion of the reinforcement body not covered with protective layer. The reinforcement body is prevented from lifting away from the inner layer when the catheter is bent even without increasing the outer diameter of the reinforcement body.

7 Claims, 8 Drawing Sheets

(56) References Cited

U.S. PATENT DOCUMENTS

| | | | | |
|---|---|---|---|---|
| 4,705,511 A * | 11/1987 | Kocak | A61M 25/005 | 604/167.04 |
| 4,985,019 A * | 1/1991 | Michelson | A61B 6/12 | 128/DIG. 26 |
| 5,078,684 A * | 1/1992 | Yasuda | A61F 2/94 | 604/531 |
| 5,084,022 A * | 1/1992 | Claude | A61M 25/09 | 600/585 |
| 5,163,921 A * | 11/1992 | Feiring | A61M 25/0075 | 604/247 |
| 5,213,111 A * | 5/1993 | Cook | A61M 25/09 | 600/585 |
| 5,228,453 A * | 7/1993 | Sepetka | A61M 25/09 | 600/434 |
| 5,272,012 A * | 12/1993 | Opolski | A61L 29/085 | 427/2.1 |
| 5,304,205 A * | 4/1994 | Shinoda | A61L 17/145 | 427/2.31 |
| 5,344,419 A * | 9/1994 | Spears | A61B 18/245 | 606/15 |
| 5,358,493 A * | 10/1994 | Schweich, Jr. | A61M 25/0013 | 604/264 |
| 5,379,779 A * | 1/1995 | Rowland | A61M 25/09 | 600/585 |
| 5,404,887 A * | 4/1995 | Prather | A61M 25/09033 | 600/434 |
| 5,432,000 A * | 7/1995 | Young, Sr. | A61F 13/531 | 428/357 |
| 5,443,907 A * | 8/1995 | Slaikeu | A61M 25/09 | 428/375 |
| 5,507,995 A * | 4/1996 | Schweich, Jr. | A61M 25/0013 | 264/293 |
| 5,545,151 A * | 8/1996 | O'Connor | A61M 25/0045 | 138/138 |
| 5,646,076 A * | 7/1997 | Bortz | D04H 1/46 | 188/251 A |
| 5,746,717 A * | 5/1998 | Aigner | A61M 25/007 | 604/102.03 |
| 5,756,144 A * | 5/1998 | Wolff | A61L 29/085 | 427/2.1 |
| 5,820,607 A * | 10/1998 | Tcholakian | A61L 29/06 | 604/265 |
| 5,824,049 A * | 10/1998 | Ragheb | A61F 2/82 | 623/1.44 |
| 5,827,201 A * | 10/1998 | Samson | A61M 25/09 | 600/585 |
| 5,908,406 A * | 6/1999 | Ostapchenko | A61L 29/041 | 604/96.01 |
| 5,965,276 A * | 10/1999 | Shlenker | A61B 42/10 | 128/837 |
| 6,083,167 A * | 7/2000 | Fox | A61N 5/1002 | 600/439 |
| 6,086,547 A * | 7/2000 | Hanssen | A61L 31/10 | 600/585 |
| 6,203,505 B1 * | 3/2001 | Jalisi | A61L 29/085 | 600/585 |
| 6,217,566 B1 * | 4/2001 | Ju | A61M 25/005 | 604/526 |
| 6,361,557 B1 * | 3/2002 | Gittings | A61F 2/07 | 606/151 |
| 6,485,735 B1 * | 11/2002 | Steen | A61B 18/14 | 424/422 |
| 6,591,472 B1 * | 7/2003 | Noone | A61M 25/0009 | 264/171.13 |
| 6,593,255 B1 * | 7/2003 | Lawton | C03C 25/00 | 428/372 |
| 6,652,507 B2 * | 11/2003 | Pepin | A61M 25/0045 | 604/264 |
| 6,689,120 B1 * | 2/2004 | Gerdts | A61M 25/005 | 604/526 |
| 6,702,782 B2 * | 3/2004 | Miller | A61M 25/005 | 138/111 |
| 6,786,876 B2 * | 9/2004 | Cox | A61L 29/085 | 600/585 |
| 6,811,875 B2 * | 11/2004 | Kikuchi | H01B 3/00 | 174/110 A |
| 6,811,958 B2 * | 11/2004 | Iwami | A61M 25/00 | 430/320 |
| 6,817,995 B1 * | 11/2004 | Halpern | A61M 39/1011 | 604/523 |
| 6,945,970 B2 * | 9/2005 | Pepin | A61L 29/085 | 138/134 |
| 7,001,369 B2 * | 2/2006 | Griffin | A61M 25/0051 | 604/524 |
| 7,081,096 B2 * | 7/2006 | Brister | A61B 1/00082 | 600/549 |
| 7,175,607 B2 * | 2/2007 | Lim | A61M 25/1029 | 604/103.06 |
| 7,335,184 B2 * | 2/2008 | Laguna | A61L 29/085 | 604/101.02 |
| 7,651,469 B2 * | 1/2010 | Osborne | A61L 31/10 | 600/585 |
| 7,687,144 B2 * | 3/2010 | Clark | A61L 29/103 | 428/375 |
| 7,766,049 B2 * | 8/2010 | Miller | A61M 25/0053 | 138/116 |
| 7,942,581 B2 * | 5/2011 | Leonardelli | B05D 5/08 | 384/129 |
| 8,034,045 B1 * | 10/2011 | Lyons | A61M 25/0012 | 604/523 |
| 8,106,474 B2 * | 1/2012 | Yamazaki | H01L 23/5223 | 257/459 |
| 8,187,206 B2 * | 5/2012 | Kinoshita | A61M 25/09 | 600/585 |
| 8,197,424 B2 * | 6/2012 | Nabeshima | A61M 25/09 | 600/585 |
| 8,231,647 B2 * | 7/2012 | Eidenschink | A61M 25/0043 | 604/103 |
| 8,317,772 B2 * | 11/2012 | Jansen | A61M 25/005 | 604/523 |
| 8,353,868 B2 * | 1/2013 | Davies, Jr. | A61M 25/104 | 264/241 |
| 8,795,255 B2 * | 8/2014 | Jansen | A61M 25/005 | 604/527 |
| 9,028,427 B2 * | 5/2015 | Kinoshita | A61M 25/09 | 600/585 |
| 2004/0098021 A1 * | 5/2004 | Laguna | A61L 29/085 | 606/194 |
| 2008/0108974 A1 | 5/2008 | Yee Roth | | |
| 2010/0298812 A1 * | 11/2010 | Wolkenstorfer | A61M 25/0041 | 604/523 |
| 2012/0185030 A1 * | 7/2012 | Igaki | A61F 2/958 | 623/1.11 |
| 2016/0136387 A1 * | 5/2016 | Otake | A61M 25/0012 | 604/526 |

FOREIGN PATENT DOCUMENTS

| | | |
|---|---|---|
| JP | H07-323090 A | 12/1995 |
| JP | 3659664 B2 | 6/2005 |
| JP | 2011-019664 A | 2/2011 |
| JP | 2012-100829 A | 5/2012 |
| JP | 2012-249811 A | 12/2012 |
| JP | 2012-249812 A | 12/2012 |
| WO | 2014/189828 A1 | 11/2014 |

OTHER PUBLICATIONS

Jun. 5, 2018 Office Action issued in Japanese Patent Application No. 2015-157962.

May 21, 2019 Office Action issued in Japanese Patent Application No. 2018-140873.

* cited by examiner

CATHETER AND BALLOON CATHETER

CROSS REFERENCE TO RELATED APPLICATION

This application claims priority to Japanese Application No. 2015-157962, which was filed on Aug. 10, 2015, the entire contents of which are incorporated herein by reference.

BACKGROUND

The disclosed embodiments relate to a medical device. Specifically, the disclosed embodiments relate to a catheter and a balloon catheter.

A conventional catheter is described in Japanese Patent Application Laid-Open No. 2012-100829. The catheter comprises an elongated tubular main body including an inner layer, a coil layer (a reinforcement body) formed with a wire material wound around the outer periphery of the inner layer, and an outer layer covering the coil body.

Further, Japanese Patent No. 3659664 describes a medical tube comprising an inner layer, a reinforcement layer adhered to the outside of the inner layer, and an outer layer adhered to the outside of the reinforcement layer. The reinforcement layer is a coil layer having a first coil and a second coil.

However, the catheter according to Japanese Patent Application Laid-Open No. 2012-100829 and the medical tube according to Japanese Patent No. 3659664 described above have the following problem: a reinforcement body formed of a coil tends to experience springback after bending, wherein the bend is partially released and an end of the coil "lifts" away from the inner layer.

Japanese Patent Application Laid-Open No. 2012-249812 attempts to solve the above problem. Japanese Patent Application Laid-Open No. 2012-249812 describes an outer catheter comprising an inner layer, an outer layer, and an intermediate layer (a reinforcement body) that is formed of a linear object and sandwiched between the inner layer and the outer layer, wherein a distal end of the intermediate layer is covered with a contrasting ring (a protective layer).

However, in the case of the outer catheter according to Japanese Patent Application Laid-Open No. 2012-249812, the outer diameter of the catheter is disadvantageously larger at the distal end of the intermediate layer because the contrasting ring is thick.

SUMMARY

An objective of the disclosed embodiments is to provide a catheter and a balloon catheter in which a reinforcement body is prevented from lifting away from an inner layer without increasing the outer diameter at an end of the reinforcement body.

A catheter of the disclosed embodiments comprises a tubular inner layer, a reinforcement body disposed around the outer periphery of the inner layer, a protective layer partially covering the outer periphery of the reinforcement body, and an outer layer covering at least the outer periphery of the protective layer, wherein the protective layer covers at least the outer periphery of one end of the reinforcement body, and the one end of the reinforcement body covered with the protective layer is buried deeper in a side of the inner layer relative to a portion of the reinforcement body not covered with the protective layer.

In the aforementioned configuration, the reinforcement body is prevented from "lifting" away from the inner layer when bent because the end of the reinforcement body is covered with the protective layer. Further, the end of the reinforcement body covered with the protective layer is buried and constrained in the inner layer. Therefore, movement of the reinforcement layer relative to the inner layer is controlled as compared with an unburied portion of the reinforcement body, and the reinforcement layer is even more reliably prevented from lifting away from the inner layer. Furthermore, the end of the reinforcement body is buried in the inner layer, and thus the outer diameter of the whole catheter at that portion is no larger than the diameters of other portions of the catheter.

In addition, the protective layer is desirably configured with a resin. A catheter having the aforementioned configuration can be easily manufactured and processed. In addition, the catheter is generally prevented from breaking if a low stiffness resin is used for the protective layer.

Further, the protective layer is desirably configured with a heat-shrinkable resin tube, simplifying the manufacturing process.

In addition, the outer layer is preferably configured with a resin, and the resin of the protective layer has a higher melting point than that of the outer layer. According to the aforementioned configuration, the protective layer can be prevented from becoming thinner when the outer layer is fused to the inner layer. Therefore, the strength of the protective layer can be assured, and there is less risk that the end of the reinforcement body will lift away from the inner layer.

In addition, the protective layer desirably covers both a distal end and a proximal end of the reinforcement body. According to the aforementioned configuration, the reinforcement body is even more reliably prevented from lifting away from the inner layer due to springback, which in turn prevents the outer diameter at each of the distal and proximal ends of the reinforcement body from becoming larger.

Further, a balloon catheter according to the disclosed embodiments comprises the above catheter and a balloon joined to the outer periphery of the outer layer in the above catheter. According to the aforementioned configuration the reinforcement body is prevented from lifting away from the inner layer in the balloon catheter without requiring an increase in the outer diameter at the distal end of the reinforcement body.

DETAILED DESCRIPTION OF EMBODIMENTS

Below, catheters according to the disclosed embodiments will be described in detail. However, the present invention shall not be limited to the embodiments described below, and modifications in design can be made appropriately. In FIGS. 1 to 8, the left side corresponds to a distal end that is to be inserted into the body, and the right side corresponds to a proximal end that is to be operated by an operator such as a physician.

Figure 1:
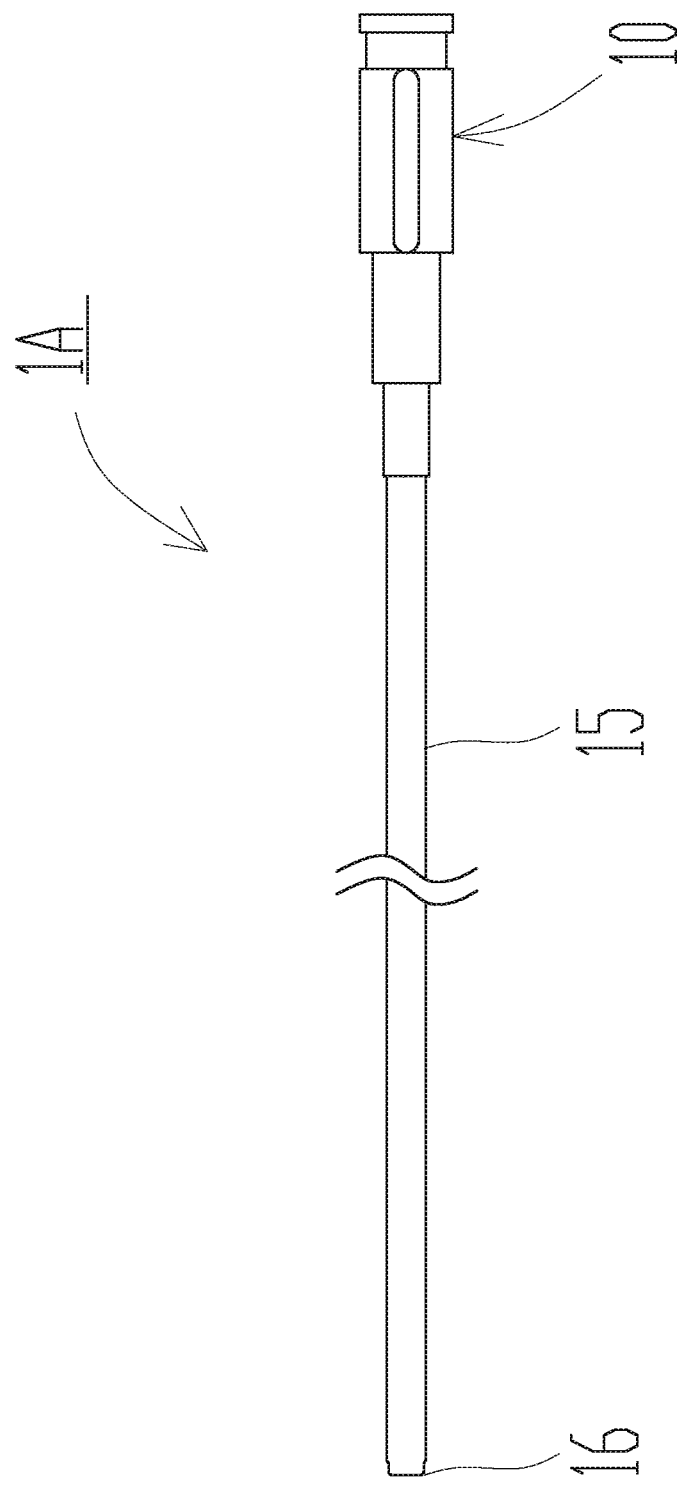
FIG. 1 shows a top view of a catheter according to the disclosed embodiments.

As shown in FIG. 1, a catheter 1A has an operating portion 10 to be operated by an operator, a main body 15 extending from the operating portion 10, and a distal end part 16 located at the distal end of the main body 15.

Figure 2:
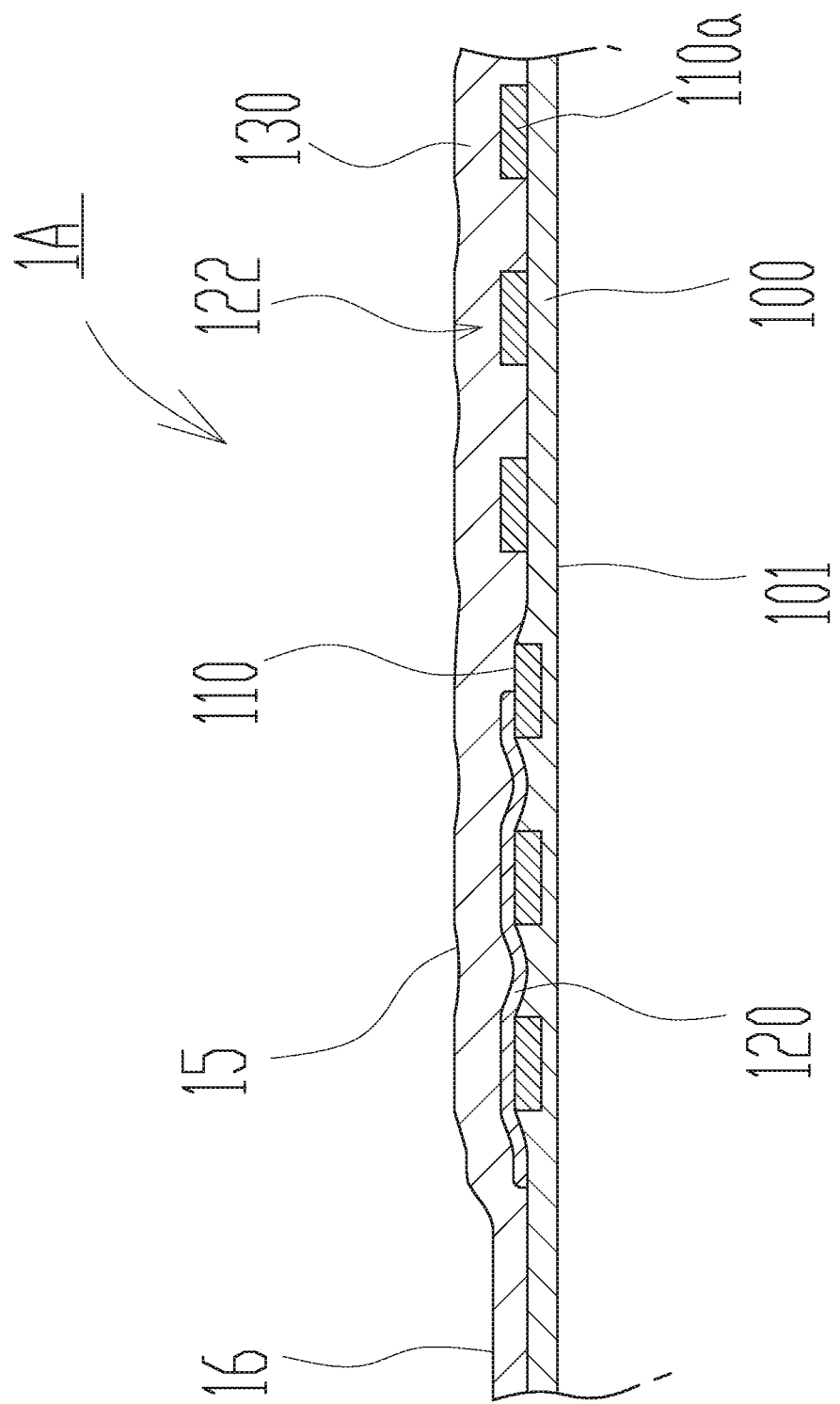
FIG. 2 shows an enlarged partial cross-sectional view of the catheter of FIG. 1.

More specifically, the catheter 1A has a tubular inner layer 100 as shown in FIG. 2. The inner layer 100 comprises an inner lumen 101 through which a guide wire or the like is to be inserted.

Further, a coil body 110 is disposed at the outer periphery of the inner layer 100 as a reinforcement body in which a wire 110a is spirally wound.

Moreover, a protective layer 120 is formed on the outer periphery of a distal portion (a distal end part) of the coil body 110 such that the distal portion of the coil body 110 is covered with the protective layer 120. Note that proximal to the distal portion of the coil body 110, an unprotected portion 122 is formed that is not covered with the protective layer 120. Therefore, the protective layer 120 partially covers the outer periphery of the coil body 110.

Further, in the portion of the coil body 110 covered with the protective layer 120, the wire 110a of the coil body 110 is buried in the inner layer 100 (that is, the coils of the coil body project into the inner layer 100). In contrast, the wire 110a of the coil body 110 at the unprotected portion 122 is not buried in the inner layer 100.

In addition, an outer layer 130 is formed on the outer periphery of each of the inner layer 100, the coil body 110, and the protective layer 120; and the inner layer 100, the coil body 110, and the protective layer 120 are covered with the outer layer 130.

Further, a coating layer may cover the outer periphery of the outer layer 130.

Note that the distal end part 16 of the catheter 1A includes a part of the inner layer 100, a part of the coil body 110, the protective layer 120, a part of the unprotected portion 122, and a part of the outer layer 130.

Note that the inner layer 100 preferably comprises a resin such as polyethylene, polyurethane, polyamide, polyamide elastomer, polyolefin, polyester, or polyester elastomer. Further, in order to reduce friction between the inner lumen 101 and a guide wire or the like that is to be inserted into the inner lumen 101, the inner periphery of the inner layer 100 may be coated with a fluorine-based resin such as polytetrafluoroethylene (PTFE).

Moreover, the coil body 110 preferably comprises stainless steel (SUS 304), tungsten, or a superelastic alloy such as a Ni—Ti alloy. Note that the cross-sectional shape of the wire 110a of the coil body 110 is not limited to a rectangular shape, and it may be a circular shape, an elliptical shape, a polygonal shape, or the like.

Further, the protective layer 120 desirably comprises a heat-shrinkable resin tube having a melting point higher than the outer layer 130. Preferred resins for the tube are, for example, polyethylene terephthalate resin (PET resin), polyimide resin, or polyether ether ketone resin (PEEK resin). By using a material having a higher melting point, the protective layer 120 is prevented from becoming thinner when fusing the outer layer 130 to the inner layer 100. As a result, the strength of the protective layer 120 can be assured, reducing the risk that the distal portion (and thus the distal end) of the coil body 110 will lift away from the inner layer 100. Note that the protective layer 120 may comprise a metal material, but preferably comprises a resin in view of easier manufacturing and processing of the catheter 1A. Further, the catheter 1A is generally prevented from breaking if a low stiffness resin is used for the protective layer 120.

Moreover, the outer layer 130 desirably comprises a resin such as polyethylene, polyurethane, polyamide, polyamide elastomer, polyolefin, polyester, or polyester elastomer.

In the catheter 1A having the protective layer 120, the coil body 110 is prevented from lifting away from the inner layer 100 due to springback when the catheter 1A is bent. Further, the distal portion of the coil body 110 covered with the protective layer 120 is buried in the inner layer 100, and the periphery of the wire 110a of the coil body 110 at that portion is covered with the protective layer 120. Therefore, the distal portion of the coil body 110 is constrained by the inner layer 100, and more resistant to lifting away from the inner layer 100 when bent. Furthermore, the catheter 1A does not have a larger outer diameter where the protective layer 120 is included because the distal portion of the coil body 110 is buried in the inner layer 100.

In addition, the flexibility of the catheter 1A as an elastic body is not impaired because the wire 110a of the coil body 110 at the unprotected portion 122 is not buried in the inner layer 100. Compared with a case where the full length of the coil body 110 is buried in the inner layer 100 without providing the unprotected portion 122, the catheter 1A can more easily bend along a blood vessel or digestive organ. As a result, the catheter 1A is more resistant to breaking when inserted into a blood vessel or digestive organ.

Note that the wire 110a of the coil body 110 may be completely buried in the inner layer 100, or may be partially buried in the inner layer 100.

Figure 3A:
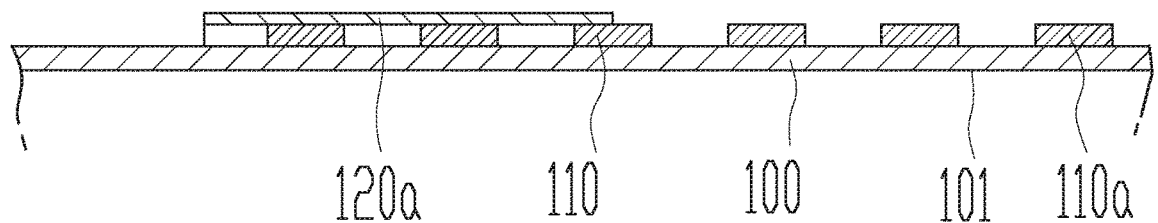
FIGS. 3A to 3C show schematic diagrams illustrating a manufacturing process of the catheter of FIG. 1.

Below, a method for manufacturing the catheter 1A will be described briefly. First, as shown in FIG. 3A, the coil body 110 is wound around the outer periphery of the inner layer 100, and a heat-shrinkable resin tube 120a is placed on the outer periphery of the distal portion of the coil body 110.

Figure 3B:
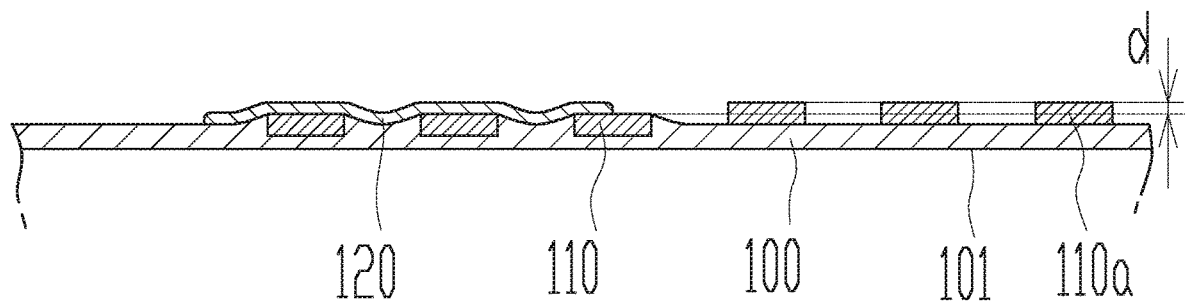

Next, the heat-shrinkable resin tube 120a is heated and shrunk to form the protective layer 120, and at the same time, the wire 110a in the distal portion of the coil body 110 is pressed against the side of the inner layer 100 to be buried to a depth d as shown in FIG. 3B.

Figure 3C:
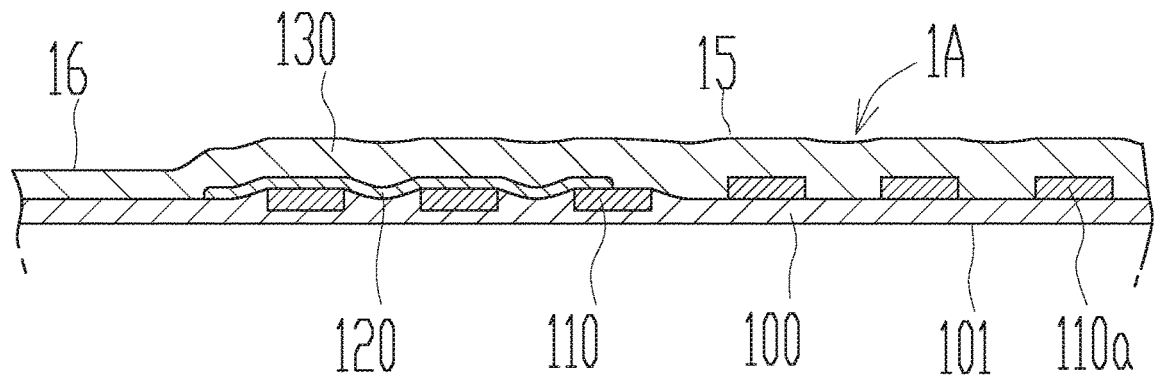

Then, the outer layer 130 is fused to the outer periphery of each of the inner layer 100, the coil body 110, and the protective layer 120 as shown in FIG. 3C. Note that the outer layer 130 may be formed after performing thermal shrinkage of the heat-shrinkable resin tube to form the protective layer 120, or may be formed upon performing the thermal shrinkage.

The manufacturing process can be simplified in a case where the heat-shrinkable resin tube 120a is used for the protective layer 120 because the protective layer 120 can be formed simultaneously to when the outer layer 130 is fused with the inner layer 100.

Note that the above manufacturing method is merely an example, and a different manufacturing method may be used, of course. For example, the protective layer 120 may be formed on the outer periphery of the coil body 110 after the coil body 110 is buried in the side of the inner layer 100 by a so-called swaging process. Alternatively, a tube comprising a resin material or a metal material as the protective layer 120 may be placed on the outer periphery of the distal portion of the coil body 110 instead of the heat-shrinkable resin tube 120a. Then, the wire 110a of the coil body 110 may be buried in the side of the inner layer 100 by the swaging process.

Figure 4:
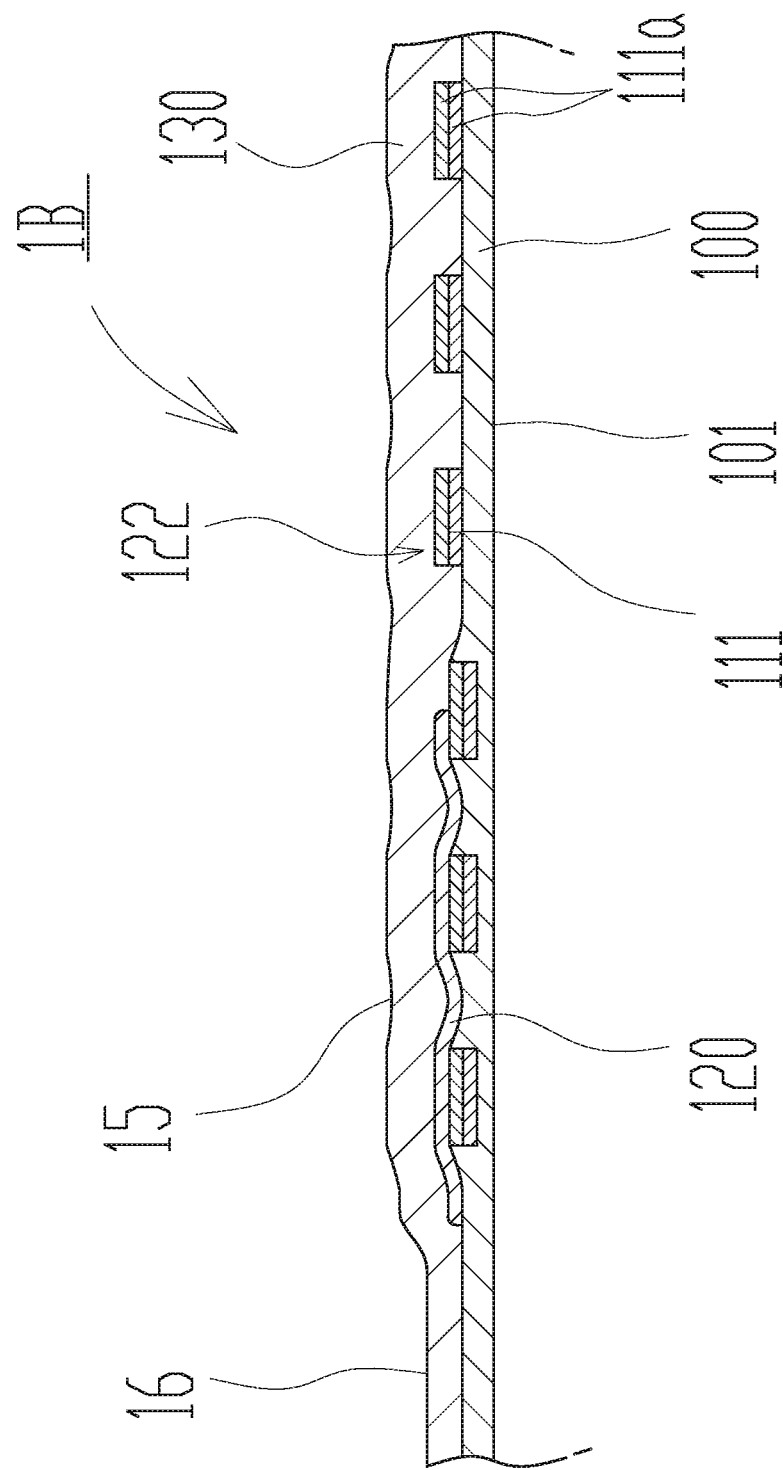
FIG. 4 shows an enlarged partial cross-sectional view of a catheter according to the disclosed embodiments.

A catheter 1B will be described with reference to FIG. 4. Note that the same reference numbers are assigned to structures similar to those in FIGS. 1 to 3C, and the descriptions thereof are omitted.

The catheter 1B comprises a braid 111 instead of the coil body 110 of catheter 1A. The braid 111 includes two or more wires 111a woven in a mesh-like manner and serves as a reinforcement body. Note that the multiple wires 111a of the braid 111 preferably comprise stainless steel (SUS 304), tungsten, or a superelastic alloy such as a Ni—Ti alloy. The cross-sectional shape of each of the two or more wires 111a of the braid 111 are not limited to being rectangular, and they may be circular, elliptical, polygonal, or the like.

In addition, the distal portion of the braid 111 is covered with the protective layer 120, and further, the wires 111a of the braid 111 covered with the protective layer 120 are buried in the inner layer 100.

Again, by virtue of the protective layer 120, the braid 111 is prevented from lifting away from the inner layer 100 due to springback when the catheter 1B is bent. Further, the distal portion of the braid 111 that is covered with the protective layer 120 is buried in the inner layer 100, and is thus constrained by being covered with the inner layer 100. Therefore, the braid 111 can be even further prevented from lifting away from the inner layer 100 when bent. Moreover, the catheter 1B does not have a larger outer diameter where the protective layer 120 is included because the distal portion of the braid 111 is buried in the inner layer 100. Further, the flexibility of the catheter 1B as an elastic body is not impaired because the wires 111a of the braid 111 at the unprotected portion 122 are not buried in the inner layer 100. The catheter 1B can more easily bend along a blood vessel or digestive organ as compared with a case where the full length of the braid 111 is buried in the inner layer 100 without forming the unprotected portion 122. As a result, the catheter 1B is more resistant to breaking when the catheter 1B is inserted into a blood vessel or digestive organ.

Figure 5:
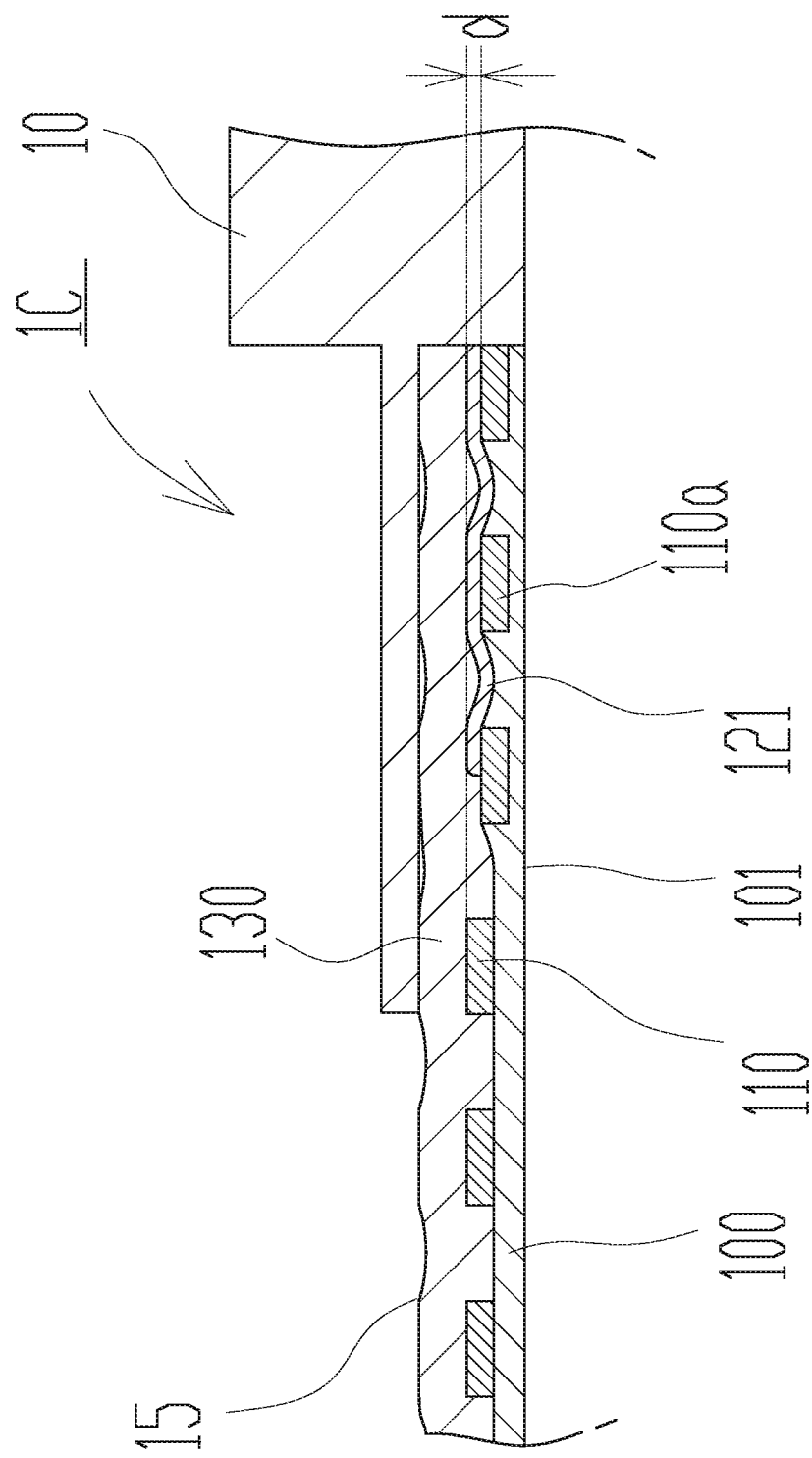
FIG. 5 shows an enlarged partial cross-sectional view of the catheter of FIG. 4.

A catheter 1C will be described with reference to FIG. 5. Note that the same reference numbers are assigned to structures similar to those in FIGS. 1 to 4, and the descriptions thereof are omitted.

In the catheter 1C, a protective layer 121 is also formed on the outer periphery of a proximal portion (a proximal end part) of the coil body 110 in addition to the distal portion of the coil body 110. Further, the proximal portion of the coil body 110 is buried in the side of the inner layer 100 to a depth d under the protective layer 121.

According to the aforementioned configuration, the coil body 110 can be prevented from lifting away from the inner layer 100 at both the distal portion and the proximal portion of the coil body 110. Further, the catheter 1C does not have a larger outer diameter at the distal portion or the proximal portion of the coil body 110 because the coil body 110 is buried in the inner layer 100 at these portions.

Figure 6:
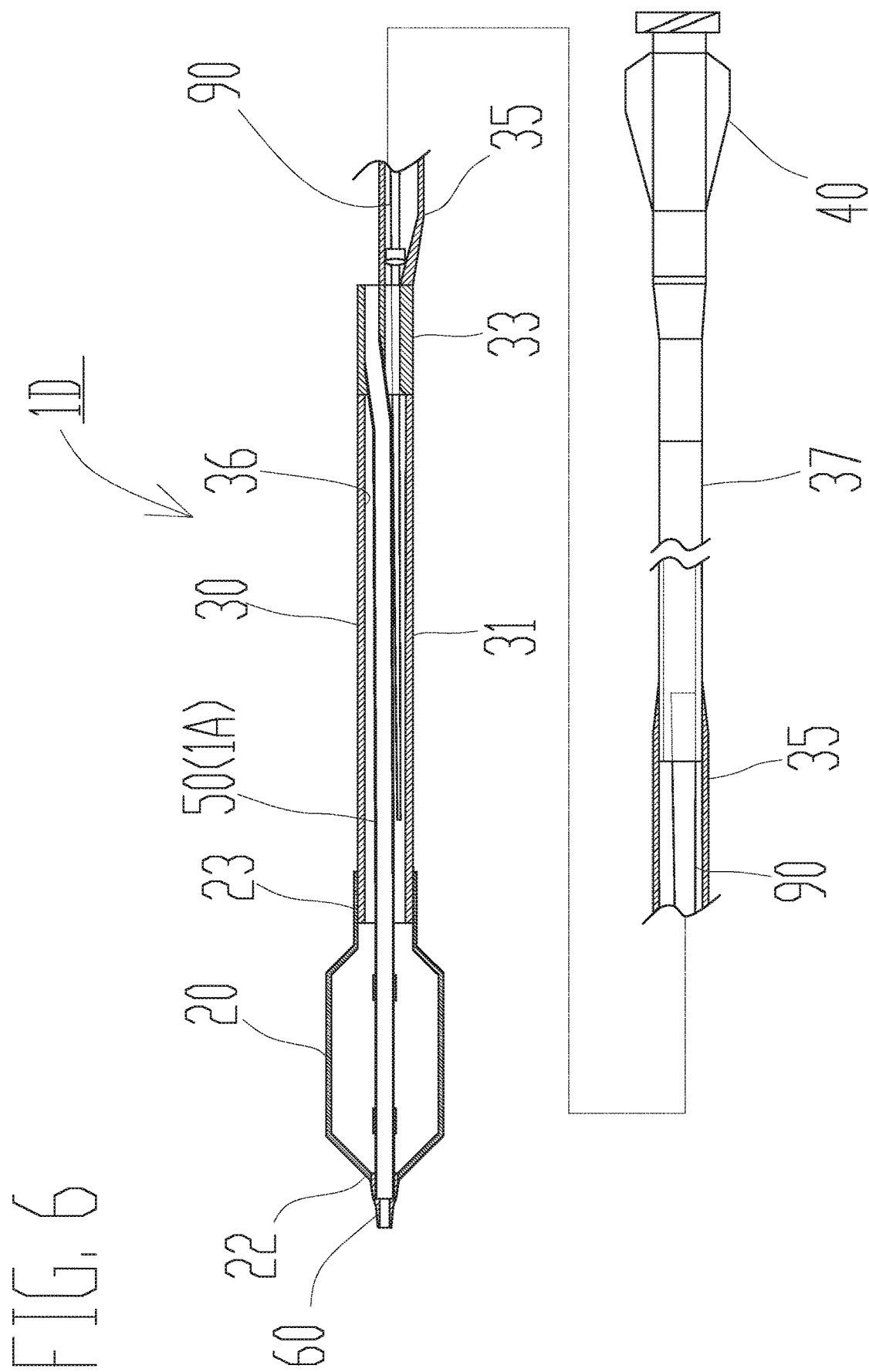
FIG. 6 shows a partial cross-sectional top view of a balloon catheter according to the disclosed embodiments.

A balloon catheter 1D will be described with reference to FIG. 6. Note that the same reference numbers are assigned to structures similar to those in FIGS. 1 to 5, and the descriptions thereof are omitted. The balloon catheter 1D may be used for treating a stenosis site in a blood vessel of the heart, for example.

The balloon catheter 1D comprises an inner shaft 50 corresponding to the catheter 1A. The balloon catheter 1D further comprises a balloon 20, an outer shaft 30, a connector 40, a tip 60, and a core wire 90.

The balloon 20 functions to expand a stenosis site, and comprises a resin material. The balloon 20 has a distal end attachment part 22 at the distal end, and a proximal end attachment part 23 at the proximal end. The distal end attachment part 22 is joined to a distal end of the inner shaft 50 through the tip 60, and the proximal end attachment part 23 is joined to a distal end of the outer shaft 30.

The outer shaft 30 functions to supply a fluid, and comprises a tubular member constituting an inflation lumen 36 for supplying the fluid. Further, the outer shaft 30 has a distal end outer shaft portion 31, a guide wire port portion 33, a middle outer shaft portion 35, and a proximal end outer shaft portion 37 in that order from the distal end. Note that the distal end outer shaft portion 31, the middle outer shaft portion 35, and the inner shaft 50 are joined at the guide wire port portion 33.

Figure 7:
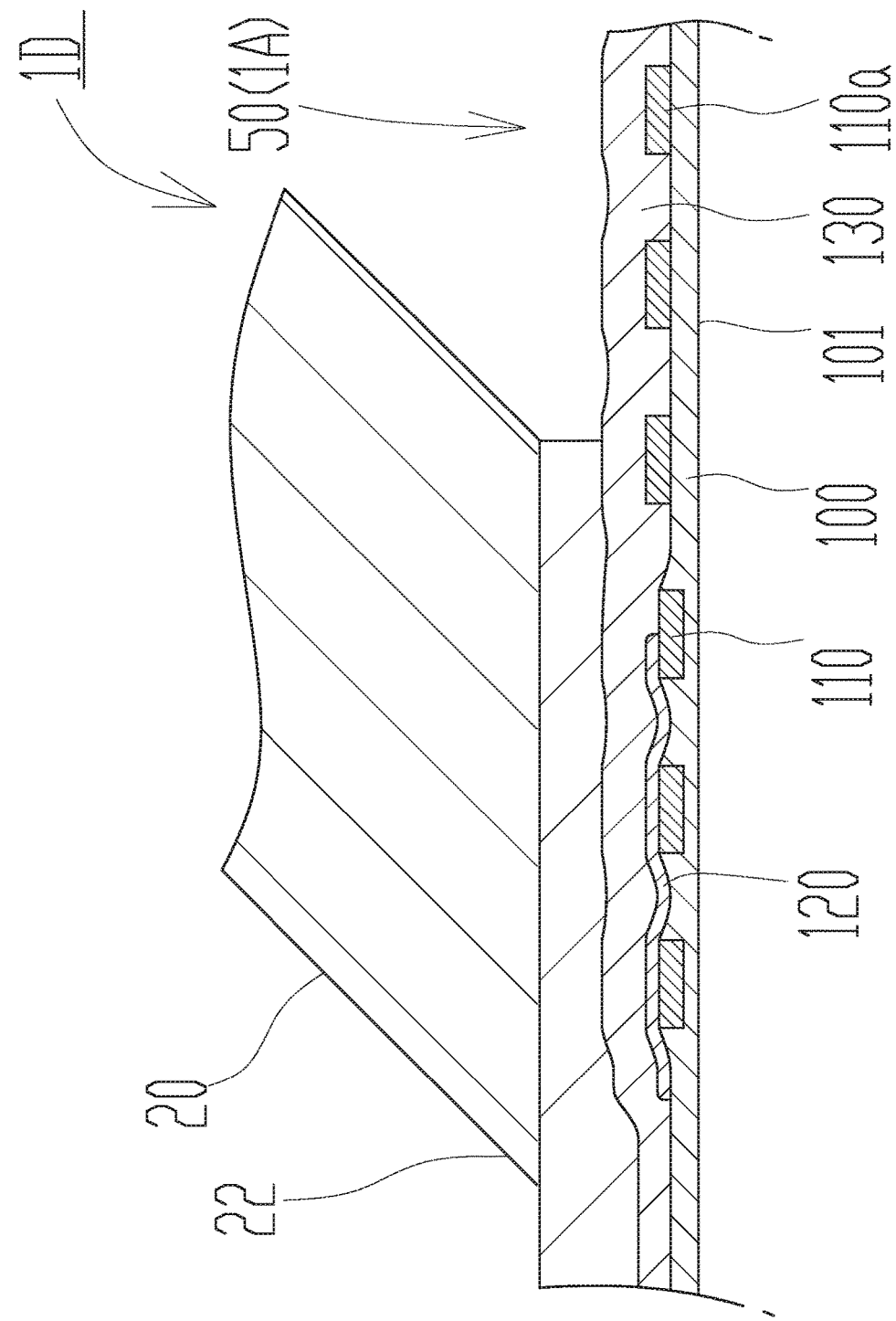
FIG. 7 shows an enlarged partial cross-sectional view of the balloon catheter of FIG. 6.

As shown in FIG. 7, the inner shaft 50 of the balloon catheter 1D in the aforementioned configuration corresponds to the catheter 1A in which the distal portion of the coil body 110 is prevented from lifting away from the inner layer 100. Therefore, the distal portion of the coil body 110 is effectively prevented from lifting away from the inner layer 100 in the balloon catheter 1D, which might otherwise occur because the end of the coil body 110 has pressure applied to it in the direction of the outer periphery due to a contrast agent, a saline solution or the like when a balloon 20 is inflated.

A balloon catheter 1E will be described with reference to FIG. 8. Note that the same reference numbers are assigned to structures similar to those in FIGS. 1 to 7, and the descriptions thereof are omitted.

Figure 8:
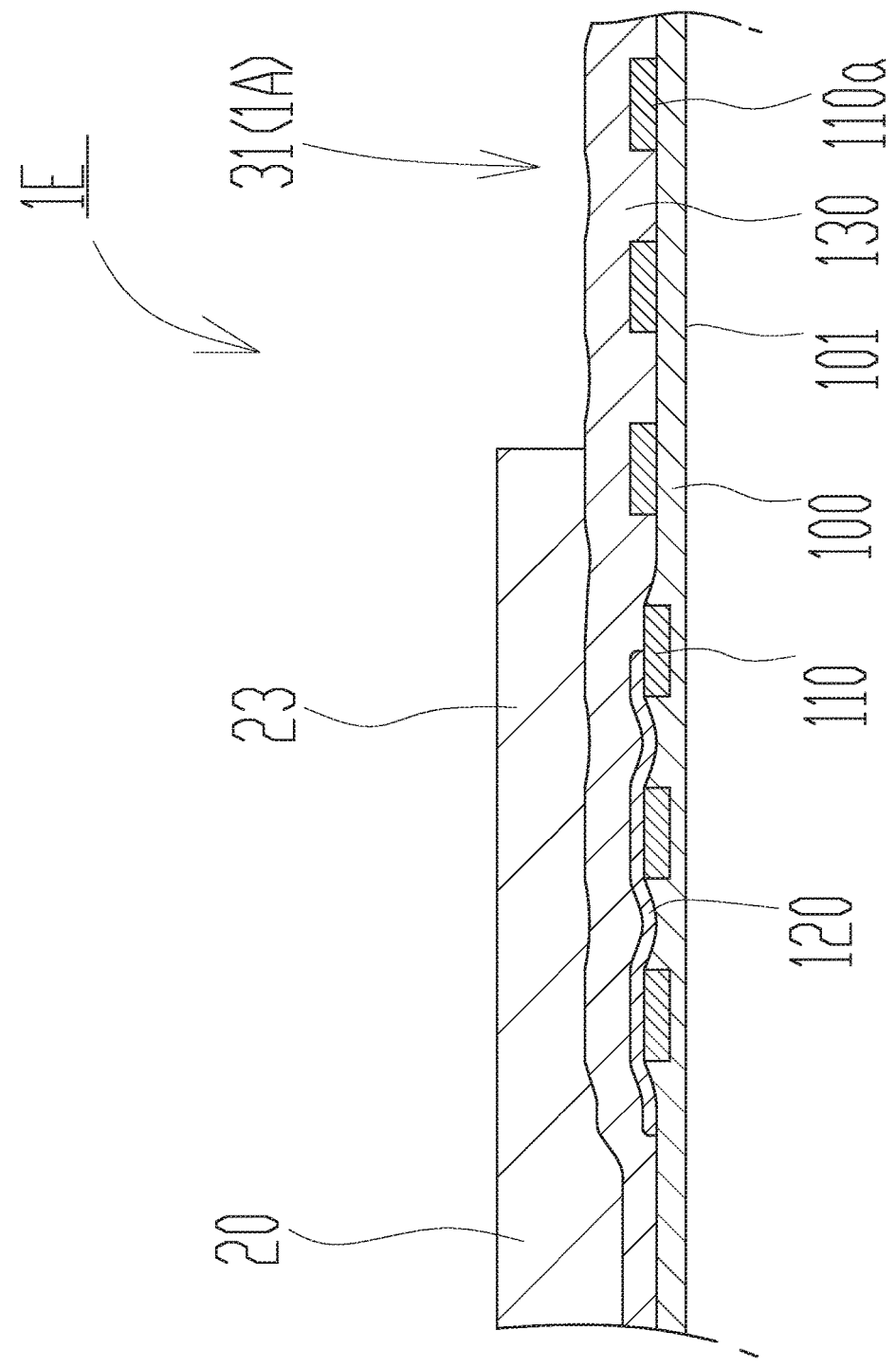
FIG. 8 shows an enlarged partial cross-sectional view of a balloon catheter according to the disclosed embodiments.

As shown in FIG. 8, the distal end outer shaft portion 31 (as opposed to the inner shaft 50) of the balloon catheter 1E corresponds to the catheter 1A. Again, according to the aforementioned construction, the distal portion of the coil body 110 is prevented from lifting away from the inner layer 100 in the balloon catheter 1E.

Note that the present invention shall not be limited to the embodiments described above, and a wide range of modifications in dimensions and shapes of components can be made appropriately.

Further, the catheter 1A is used as the inner shaft 50 and the distal end outer shaft portion 31 in balloon catheters D and E, but other configurations are possible. For example, the catheter 1B may be used as the inner shaft 50 or the distal end outer shaft portion 31, or the catheter 1C may be used as the inner shaft 50 or the distal end outer shaft portion 31.

Furthermore, in embodiments described above, the coil body 110 and the braid 111 as the reinforcement bodies are not at all buried in the inner layer 100 at the unprotected portion 122, which is not covered with the protective layer 120; however, other configurations are possible. At the unprotected portion 122, the coil body 110 and the braid 111 as the reinforcement bodies may be partially buried in the inner layer 100 to an extent that flexibility of the catheter 1A, 1B, 1C or balloon catheter 1D, 1E as an elastic body is not lost.

What is claimed is:
1. A catheter comprising, in order from an inside of the catheter to an outside of the catheter in a radial direction:
    a hollow inner tube;
    a reinforcement body disposed around an outer periphery of the hollow inner tube;
    a protective layer partially covering an outer periphery of the reinforcement body; and
    an outer layer covering at least an outer periphery of the protective layer, wherein the protective layer covers an outer periphery of at least one of a distal-most end of the reinforcement body or a proximal-most end of the reinforcement body, and either of the distal-most end or the proximal-most end of the reinforcement body covered with the protective layer is buried deeper in the hollow inner tube in the radial direction toward a central axis of the catheter relative to a portion of the reinforcement body not covered with the protective layer.

2. The catheter according to claim 1, wherein the protective layer comprises a resin.

3. The catheter according to claim 2, wherein the outer layer comprises a resin, and the resin of the protective layer has a melting point higher than a melting point of the resin of the outer layer.

4. The catheter according to claim 1, wherein the protective layer comprises a heat-shrinkable resin tube.

5. The catheter according to claim 4, wherein the outer layer comprises a resin, and the resin of the protective layer has a melting point higher than a melting point of the resin of the outer layer.

6. The catheter according to claim 1, wherein the reinforcement body is a helical coil.

7. The catheter according to claim 1, wherein the reinforcement body is a unitary one-piece reinforcement body.

* * * * *